United States Patent
Meade

[11] Patent Number: 5,843,100
[45] Date of Patent: Dec. 1, 1998

[54] SUTURE NEEDLE GRASPING AND MANIPULATING DEVICE

[75] Inventor: John C. Meade, Walpole, Mass.

[73] Assignee: Garfield Development Corporation, Walpole, Mass.

[21] Appl. No.: 921,743

[22] Filed: Aug. 27, 1997

Related U.S. Application Data

[63] Continuation of Ser. No. 777,704, Dec. 20, 1996, abandoned.

[51] Int. Cl.$^6$ .................................................. A61B 17/04
[52] U.S. Cl. ........................... 606/147; 606/145; 606/205
[58] Field of Search ..................... 606/145, 147, 606/151, 205, 206, 207

[56] References Cited

U.S. PATENT DOCUMENTS

| | | | |
|---|---|---|---|
| 3,139,089 | 6/1964 | Schwerin | 606/147 |
| 4,370,980 | 2/1983 | Lottick . | |
| 4,621,640 | 11/1986 | Mulholian | 606/147 |
| 4,898,157 | 2/1990 | Messroghli et al. | 606/147 |
| 5,026,370 | 6/1991 | Lottick | 606/42 |
| 5,201,743 | 4/1993 | Haber et al. | 606/147 |
| 5,224,948 | 7/1993 | Abe et al. | 606/147 |
| 5,242,458 | 9/1993 | Bendel et al. | 606/147 |
| 5,257,999 | 11/1993 | Slantetz, Jr. | 606/147 |
| 5,364,408 | 11/1994 | Gordon | 606/144 |
| 5,387,221 | 2/1995 | Bisgaard | 606/147 |
| 5,403,328 | 4/1995 | Shallmon | 606/144 |
| 5,454,819 | 10/1995 | Knoepfler | 606/147 |
| 5,458,609 | 10/1995 | Gordon et al. | 606/144 |
| 5,540,704 | 7/1996 | Gordon et al. | 606/144 |
| 5,540,705 | 7/1996 | Meade et al. | 606/147 |

*Primary Examiner*—Gary Jackson
*Attorney, Agent, or Firm*—Pandiscio & Pandiscio

[57] ABSTRACT

A suture needle grasping and manipulating instrument includes first and second pivotally-connected arms each having a proximal end and a distal end, and first and second jaw assemblies or units pivotally mounted on the distal ends of the first and second arms respectively, said arms being disposed so as to permit relative pivotal movement thereof between a first closed jaw position wherein the jaw assemblies or units are adjacent one another and a second open position wherein the jaw assemblies or units are spaced from one another far enough to permit a needle to be inserted therebetween. The device further includes first selectively-operable means for causing said relative pivotal movement of said arms and second selectively-operable means for pivoting said jaw assemblies or jaw units relative to said arms. The jaw units have jaws that are adapted to releasably grasp and retain therebetween a curved suture needle, whereby pivotal movement of the jaw assemblies or units while in the first closed position causes the suture needle to swing in a corresponding direction for a stitching operation.

21 Claims, 10 Drawing Sheets

SUTURE NEEDLE GRASPING AND MANIPULATING DEVICE

This application is a continuation of application Ser. No. 08/777,704 filed on Dec. 20, 1996, now abandoned.

BACKGROUND OF THE INVENTION

1. Field of the Invention

This invention relates to surgical instruments and is directed more particularly to a suture needle grasping and manipulating device for suturing tissue at a surgical site.

2. Description of the Prior Art

Surgical procedures can be distinguished as "open" or "closed". In general and as used herein, the term "open surgery" applies to surgical procedures in which a surgeon accesses an interior surgical site by making a relatively large incision in a patient's body, i.e., an incision large enough to reveal the surgical site to the naked eye. By way of example, certain cardiovascular and abdominal surgical procedures are conducted on an "open" basis. Closed surgical procedures are those designed to be minimally invasive wherein the surgeon (a) makes a small incision, i.e., too small to reveal an interior surgical site to the naked eye, (b) inserts a cannula to serve as a passageway to the surgical site, and (c) inserts an endoscope through the cannula for viewing of the surgical site. Additional cannulas can be inserted through small incisions, under endoscopic view, to act as passageways or channels for various surgical instruments, i.e., forceps, graspers, scissors, suturing devices, etc. required to execute the desired procedure. Closed (minimally invasive) surgical procedures include, but are not limited to, procedures involving the abdominal area ("laparoscopic" surgery) and joints ("arthroscopic" surgery). More recently, cardiovascular surgical procedures have been developed wherein minimally invasive surgery is conducted using an endoscope to enable the surgical team to properly position and manipulate various surgical instruments.

Both open and closed surgical procedures typically involve suturing of internal tissues or organs ("internal suturing"). Open surgical procedures also involve substantial suturing to close off the incision ("external suturing"). In closed or minimally invasive surgery, e.g. laparoscopic surgery, suturing within the abdominal cavity must be accomplished in the confines of a cannula using a needle grasping and manipulating device. Suturing in both open and closed surgical procedures generally requires use of an additional tool, sometimes referred to as a "grasper", for grasping the needle and/or pulling the needle through the pierced tissue to complete a stitch and position it for a subsequent stitch.

Various instruments have been devised to hold surgical needles and drive them through body tissue for stitching purposes. Many such instruments are suitable only for open surgery wherein the surgeon often has the benefit of space in which to effect the suturing. Some suturing instruments have been devised for suturing through cannula tubes. One such instrument is disclosed in U.S. Pat. No. 4,261,640, issued Nov. 11, 1986 to James S. Mulhollan et al, wherein there is described an instrument that holds and drives a needle. Another such instrument is described in U.S. Pat. No. 5,403,328, issued Apr. 4, 1995 to Richard W. Shallman. Both the Mulkabian and Shallman instruments provide means for holding and driving a needle, but are limited in their ability to manipulate the needle and/or forcing the needle through the tissue and then positioning it for use in making another subsequent stitch.

Hence there remains a need for an improved suture needle grasping and manipulating device for either open or closed surgery wherein the device can be used to manipulate a needle with an attached suture so as to create a plurality of stitches, that is, a device which (a) is adapted to hold a suture-carrying needle and drive that needle through tissue, and (b) can be used to pull the needle completely through the tissue so as to free the needle for one or more subsequent stitching operations.

SUMMARY OF THE INVENTION

A primary object of the invention is to provide a novel instrument for grasping and manipulating a suturing needle which may be made in one form for open surgery and, alternatively, in another form for minimally invasive surgery ("M.I.S."), with both forms being adapted to facilitate forcing the needle into and through tissue so as to form one or more stitches.

Another object is to provide an instrument for the purpose stated that is adapted to grip a suture needle so that the needle is in a first selected orientation relative to the instrument, and also includes means for moving said needle laterally relative to the instrument to a second selected orientation so as to facilitate forcing the needle tip to pierce the tissue in a direction at an angle to the axis of the instrument.

The above objects and other objects that are rendered obvious hereinafter are achieved by the provision of a suture grasping and manipulating device comprising first and second arms, each having a proximal end and a distal end, first and second jaws pivotally mounted on the distal ends of the first and second arms, respectively, and means pivotally connecting the first arm to the second arm so as to permit relative pivotal movement of the arms between a first position wherein the jaws are closed and adjacent to one another and a second open position wherein the jaws are spaced from one another far enough to permit a needle to be inserted between them. The device further includes a drive lever having a distal end and a proximal end, and means pivotally connecting the distal end of the drive lever to the jaws so that axial movement of the drive lever causes relative pivotal (rotational) movement of the jaws. Means are attached to the proximal end of the drive lever for causing bi-directional axial movement of the drive lever so as to cause bi-directional pivotal (rotational) movement of the jaws relative to the first and second arms, and means are connected to the proximal ends of the arms for causing relative movement of the jaws from one to the other of the first closed position and the second open position. The jaws are adapted to releasably grasp and retain therebetween a curved suture needle, whereby pivotal (rotational) movement of the jaws while in the first closed position causes the suture needle to pivot in a corresponding direction for a stitching operation.

The above and other features of the invention, including various novel details of construction and combinations of parts, will now be more particularly described with reference to the accompanying drawings and pointed out in the claims. It will be understood that the particular devices herein described and illustrated are presented by way of illustration only and not as limitations of the invention. The principles and features of this invention may be employed in various and numerous embodiments without departing from the scope of the invention.

BRIEF DESCRIPTION OF THE DRAWINGS

Reference is now made to the accompanying drawings in which are shown illustrative embodiments of the invention, from which its novel features and advantages will be apparent.

In the drawings.

In the drawings, like components are identified by like numerals.

DESCRIPTION OF THE PREFERRED EMBODIMENTS

Figure 1:
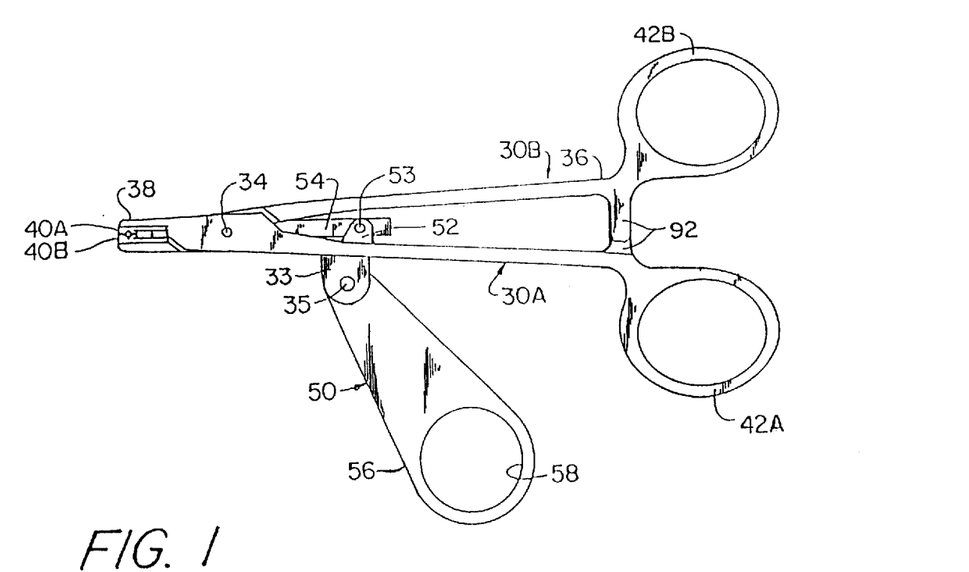
FIG. 1 is a left side elevational view of one form of suture device illustrative of a first embodiment of the invention, with the jaw assemblies or units in closed position.
Figure 2:
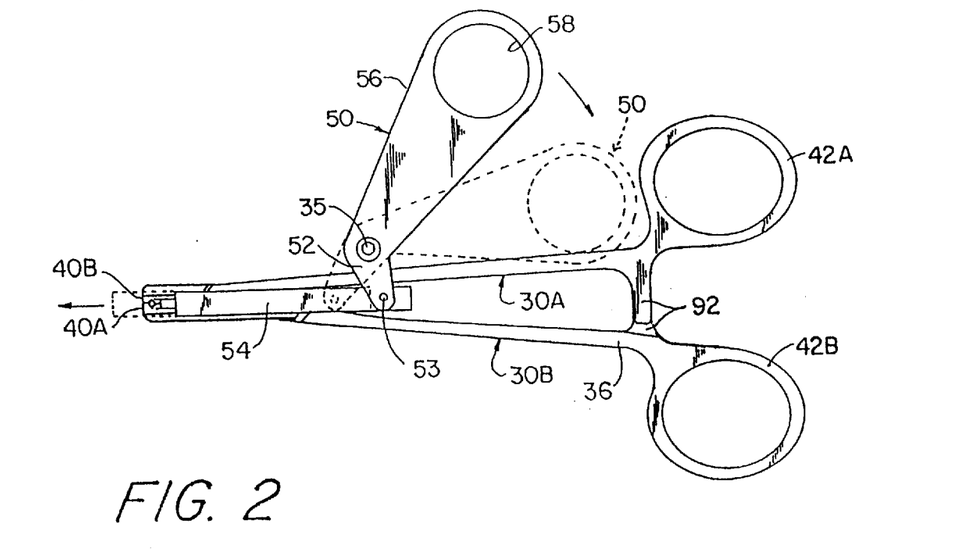
FIG. 2 is an inverted right side elevational view of the device of FIG. 1 also showing the jaw units in closed position.

FIGS. 1 and 2 illustrate a suture needle grasping and manipulating instrument designed for open surgery. The embodiment shown in FIGS. 1 and 2 includes first and second like arms 30(A and B) pivotally interconnected, as by a pivot pin 34, between their proximal and distal ends 36 and 38 respectively. Arms 30A and 30B carry two like jaw assemblies or units 40 (A and B). More specifically, a first jaw assembly 40A is mounted on the distal end 38 of the first arm 30A and a second jaw assembly 40B is mounted on the distal end 38 of the second arm 30B. Similarly a first arm operating means, such as a ring handle 42A, is fixed to the proximal end 36 of the first arm 30A and a second arm operating means, such as ring handle 42B, is fixed to the proximal end 36 of the second arm 30B. It will be apparent that the arm operating means 42A and 42B may be of any configuration suitable for gripping by the fingers of a person's hand. The jaws assemblies 40A and 40B are adapted to receive and grasp a suture needle, to be further described hereinbelow.

Pivotally attached to on one of the arms 30A, 30B is a lever 50 of a bell-crank configuration. In the illustrated embodiment, arm 30A is provided with a lateral projection 33, and lever 50 is pivotally attached to that lateral projection by a pivot pin 35. One end 52 of lever 50 is pivotally attached by a pivot pin 53 to the proximal end of a drive lever 54, while its opposite and free end 56 is provided with a grip means in the form of a ring handle 58 or some other suitable configuration, e.g., an enlarged lobe or a side projection or flange (not shown), whereby lever 50 may be moved to cause movement of a grasped needle as described hereinafter. The distal end of drive lever 54 is attached to the two jaw assemblies hereinafter described.

Figure 8:
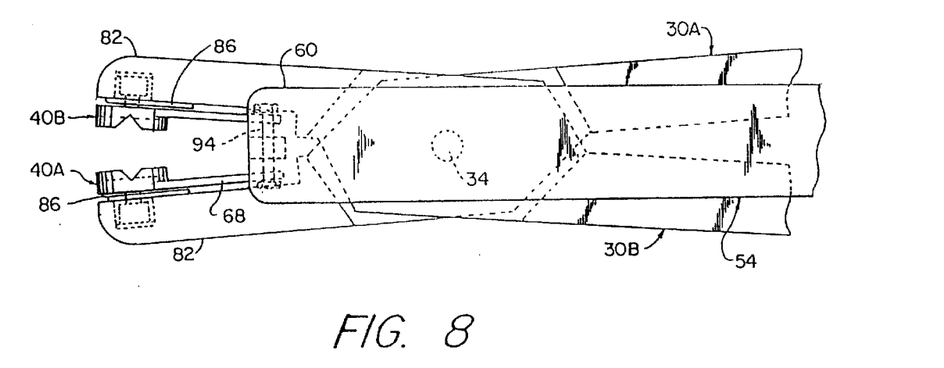
FIG. 8 is an enlarged side elevational view of a portion of the device of FIG. 2, but with the jaws shown in open position.
Figure 9:
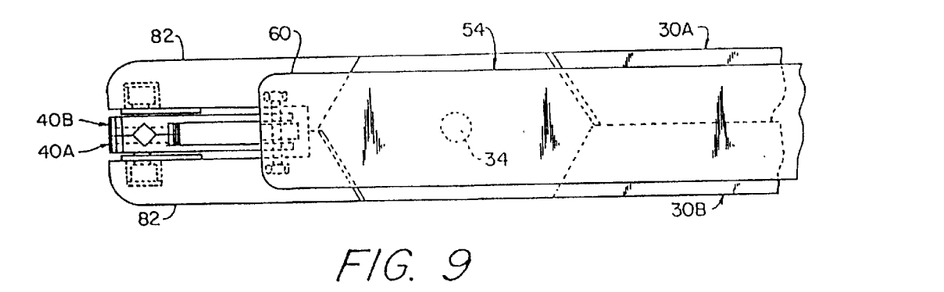
FIG. 9 is an enlarged side elevational view like FIG. 8 showing the jaws components in a closed position.

In brief, the arms 30A and 30B are manipulable by a scissors-like action, such that spreading the ring handles 42A and 42B apart from each other causes the two jaw assemblies 40, 40B to open (FIG. 8) and, conversely, moving ring handles 42A and 42b toward each other causes the jaw assemblies to close (FIG. 9). Thus, the jaw assemblies 40a and 40B may be closed to grasp a needle therebetween and opened to release the needle. Movement of lever 50 from the position shown in solid lines in FIG. 2 to the position shown in phantom in FIG. 2 operates to move the drive lever 54 axially in a forward (distal) direction, causing jaw assemblies 40A and 40B to pivot to move a curved needle laterally of the instrument in a scythe-like sweep, as will be discussed in detail hereinbelow. Opposite movement of lever 50 causes reverse rotational movement of jaw units 40A and 40B.

Figure 3:
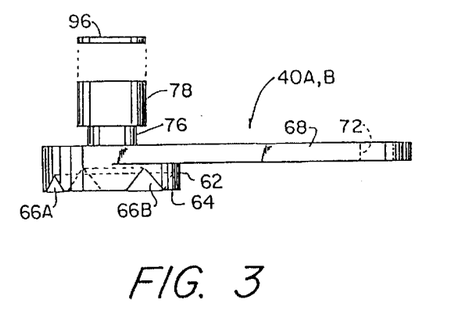
FIG. 3 is an exploded side elevational view of two jaw components of the device of FIG. 1.
Figure 4:
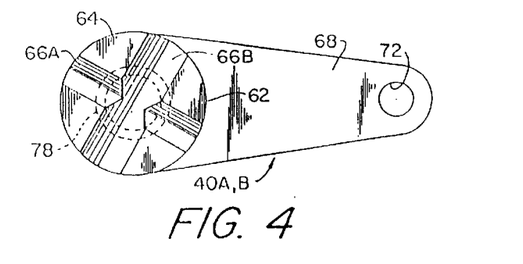
FIG. 4 is a bottom plan view of the jaw unit of FIG. 3.

FIGS. 3 and 4 illustrate details of one of the two like jaw assemblies or units 40 (A or B). As shown, each jaw assembly 40 includes a disc-shaped needle holder portion or jaw 62 having in a face 64 thereof two V-shaped grooves 66(A and B) that intersect one another, preferably at a right angle to one another. Grooves 66A and 66B are provided to facilitate secure grasping of a needle. The jaws 62 are disposed so that each of the groove 66A and 66B on one jaw can be aligned with the corresponding groove on the opposite jaw, each pair of aligned grooves forming a separate channel 48 for receiving a suture needle. Each jaw assembly also includes a link or lever arm 68 which is attached to jaw 62. Lever arm 68 is preferably formed as an integral extension of the jaw 62 to which it is attached. Lever arm 68 extends radially from the center axis of jaw 62 in a plane substantially parallel to the plane of face 64. The outer end of link 68 is provided with a hole 72 therethrough. Each jaw assembly 40 also comprises a pivot stud 76 having an enlarged head 78 at its opposite end. Stud 76 extends at a right angle to face 64 and is axially aligned with the center point of jaw 62.

Figure 5:
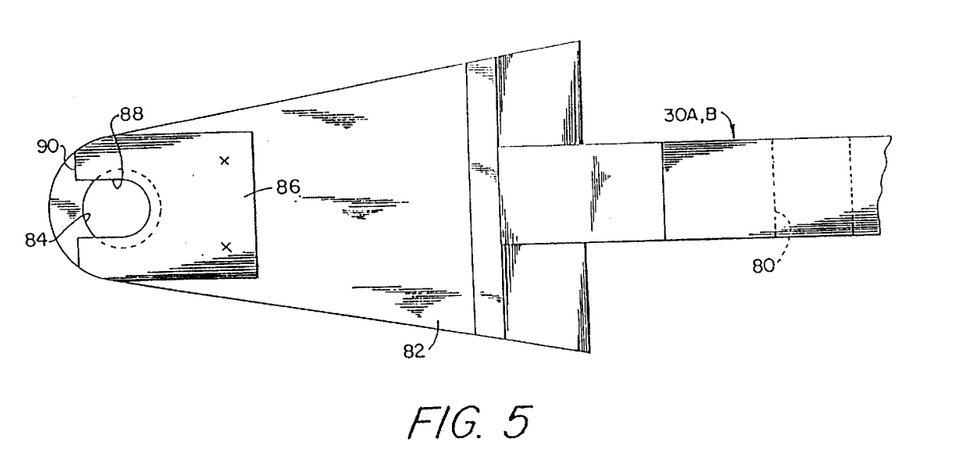
FIG. 5 is a top plan view of a portion of an arm component of the device of FIG. 1, including a portion of the jaw component of FIG. 3.
Figure 6:
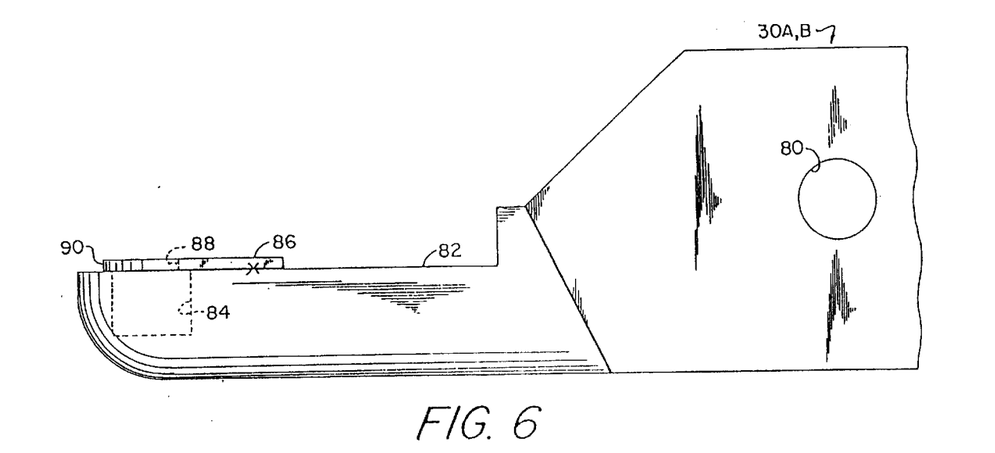
FIG. 6 is a side elevational view of the portion of the arm component shown in FIG. 5.

FIGS. 5 and 6 show a distal portion of one of the arms 30 (A and B) and the associated jaw assembly 40 (A and B). Each arm 30 (A and B) is provided with a hole 80 to accommodate pivot pin 34 (FIG. 1). Although not shown, it is to be understood that pivot pin 34 may have a head on each end to captivate the associated arms 30, with the pin being rotatable on its axis relative to both arms. Alternatively, for example, pivot pin 34 could be fixed to one of the arms 30A and rotatable relative to the other arm 30B, with the pivot pin having means thereon to captivated arm 30B so as to maintain it in sliding contact with arm 30A.

Figure 10:
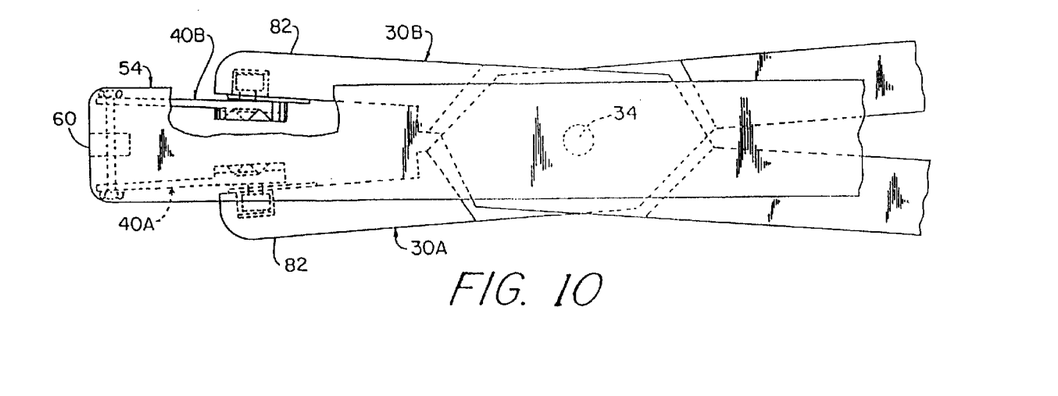
FIG. 10 is similar to FIG. 8, but showing jaw units in the same rotational position as shown in phantom in FIG. 2.

The distal end of each arm 30 (A and B) includes a jaw mounting portion 82 having a circular blind hole or cavity 84 which is configured and sized to receive the head 78 of stud 76 in a loose fit (see FIGS. 8–10). With the stud head 78 in place in 84, a plate 86 having a slot or recess 88 in a distal edge 90 thereof, is welded to the jaw mounting portion 82, with the slot 88 aligned with the hole 84. Slot 88 has a width (the dimension extending parallel to edge 90) that is less than the diameter of hole 84 and slightly larger than the diameter of stud 76, but less than the diameter of stud head 78. As a result plate 86 overlies peripheral portions of the hole 84. More importantly, plate 86 embraces stud 76 and is disposed between the jaw mounting portion 82 and the head 78 of stud 76, thereby retaining the stud head 78 in hole 84. The thickness of plate 86 is such as to permit some limited axial movement of the stud relative to mounting portion 82. It is to be understood that the above description applies to both arms 30A and 30B and both jaw assemblies.

Adjacent the ring handles 42A and 42b, the proximal ends of arms 30A and 30B are provided with lateral extensions in the form of flat posts 92 (FIGS. 1 and 2). Posts 92 are formed so that they can slidingly engage each other as the proximal ends of the arms 30A, 30B are brought toward one another. The adjacent mutually-engaging surfaces of the posts 92 (not shown) are provided with complementary ratchet teeth (not shown) which when engaged with one another cooperate to releasably lock the posts, and thereby the arms, in a selected position. It is to be understood that the ratchet teeth may take various forms, but essentially they are like the ones conventionally found on the locking portions of surgical forceps, graspers, etc. More specifically, the teeth are shaped so that when they are engaged they allow the arms to be moved in a direction so as to bring the ring handles 42A and 42B closer to one another, but prevent movement of the arms in an opposite direction. However, the arms have a certain resiliency, permitting them to be spread apart just enough to disengage the two sets of ratchet teeth from one another, thereby freeing the arms so that ring handles 42A and 42B can be moved apart far enough to free the two posts from one another, whereby the two arms are free to undergo jaw-opening movement. Such releasable locking arrangements are known in the art. See, for example, the locking arrangement illustrated in FIGS. 1 and 6 of U.S. Pat. No. 4,370,980, issued Feb. 1, 1983 to Edward A. Lottlick.

Figure 7:
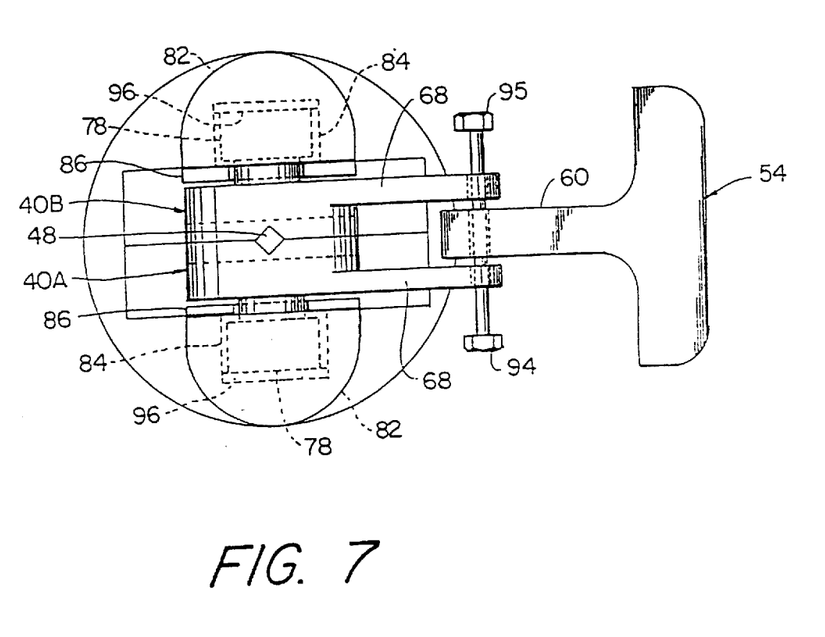
FIG. 7 is a front end elevational view of the device as positioned in FIG. 2.

Referring to FIGS. 7–9, it will be seen that the drive lever 54 is pivotally attached at its distal end 60 to the outer ends of lever arms or links 68 of the two jaw assemblies by a threaded bolt 94 and a nut 95. In practice the length of bolt 94 is such that the distance between its head and the nut 95 is greater than the distance between the outer surfaces of links 68 when the jaws are closed (FIG. 9) so as to allow some play between those links and drive lever 54. Also, the holes in links 68 for bolts 94 are slightly enlarged relative to the bolt shank, so as to allow the links to tilt relative to the bolt as shown in FIG. 10.

In FIGS. 7–10, both jaw assemblies 40A, 40B are shown mounted on their respective jaw mounting portions 82, with the cylindrical heads 78 of studs 76 rotatably retained in the holes 84 by the plates 86. Referring to FIGS. 3 and 7, flat low-friction spacers 96, e.g., spacers made of Teflon or other suitable material, may be positioned in holes 84 to assure ready movement of stud heads 78 therein. It will be apparent from FIGS. 1, 2, 7 and 8–10 that movement of drive lever 54 in a distal direction (i.e., movement of drive lever 54 leftward in FIG. 2) will cause movement of the outer ends of the links 68, which in turn will cause the jaw assemblies 40A and 40B to rotate as permitted by the rotational relationship between stud heads 78 and holes 84. Any needle (not shown in FIG. 7) held between the two jaws 62 will undergo a swinging movement as a consequence of rotation of the two jaw assemblies.

In operation, the arm operating means 42A and 42B (FIGS. 1 and 2) are manipulated to move the jaw assemblies 40A and 40B between the open jaw position (FIG. 8) and the closed jaw position (FIG. 9). Grooves 66A and 66B may be identical. Alternatively grooves 66A may have a smaller width than the grooves 66B, as shown in FIG. 4, so as to facilitate gripping the needle by its point, which is generally smaller than its blunt end. The instrument is used by placing a needle between the two open jaws in one of the grooves 66A or 66B, and then closing the jaws. The grooves 66A and 66B preferably are V-shaped so that when the jaws are closed, the round needle is subjected to a four-point gripping action by the two grooves 66A or the two grooves 66B. The four-point gripping action is sufficiently secure for suturing operations. If grooves 66A are smaller than grooves 66B, it is preferred that grooves 66A be used to grasp the pointed end of a needle and grooves 66B be used to grasp the blunt end of the needle.

Use of the instrument of FIGS. 1–10 and 12 will now be described. Assume that grooves 66A are narrower than grooves 66B and that the blunt end of a suture needle 100 (with a suture attached to its blunt end) is grasped between the jaws, with the needle's blunt end being located in the channel 48 formed by grooves 66B. Assume also that lever arm 50 is in its outer position (FIG. 1), with the jaws and the pointed end 102 of the needle in the position shown in full lines in FIG. 12. The surgeon advances the instrument to adjacent the tissue that is to be sutured, positioning the pointed end 102 of the needle at the point where the needle is to pierce the tissue to make a suture stitch, and then moves lever arm 50 from the position shown in solid lines in FIGS. 1 and 2 to the position shown in phantom lines in FIG. 2. Such movement of the lever arm 50 causes forward (distal) movement of drive lever 54, causing jaw links 68 and jaws 40A and 40B to rotate from the positions shown in solid lines in FIG. 12 to the positions shown in phantom in FIG. 12. This rotating movement causes the needle to move in a curved scythe-like sweep, forcing the pointed end 102 of the needle to penetrate through the tissue (not shown) so that the pointed end 102 projects out from the tissue and at least a portion of the blunt end of the needle is exposed.

Figure 11:
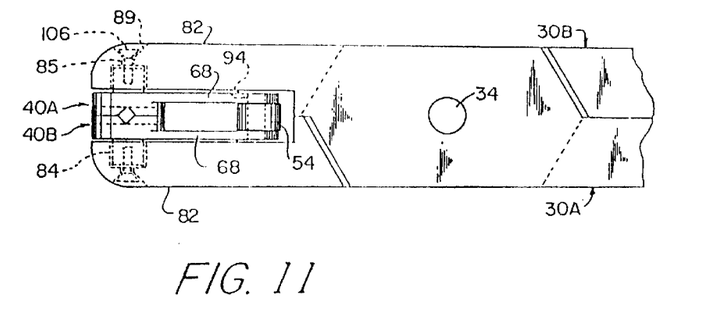
FIG. 11 is an enlarged side elevational view of a portion of an alternative embodiment of the instrument.
Figure 12:
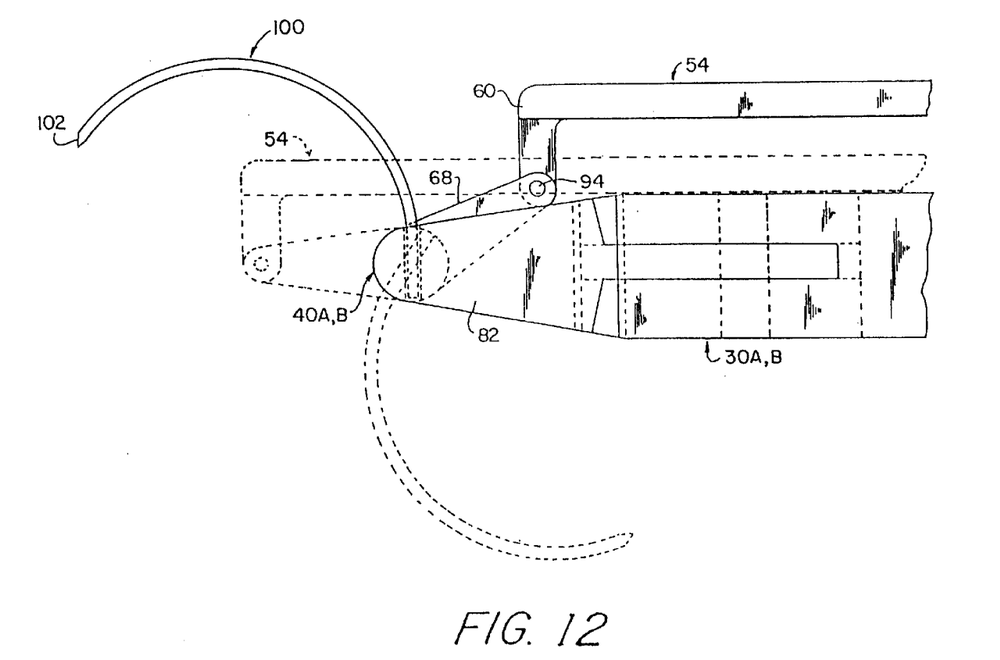
FIG. 12 is a top plan view of a portion of the embodiment of FIGS. 1–10, showing a suture needle disposed between the jaws.

As noted previously and as may be seen in FIGS. 7–10, the stud heads 78 are loosely disposed in their respective holes 84, permitting sufficient "play" of the jaw assemblies as they are moved toward and away from one another (FIGS. 8–10) and also as they rotate under the influence of driver member 54 (see also FIG. 12), so to prevent any binding of the jaw assemblies and thereby permit ready transition of the jaws to and from the various positions shown in FIGS. 8–12.

Once the point of the needle 100 is driven through the tissue, the jaws 62 are opened (FIG. 10) by manipulation of the arm operating means 42, 42B to release the needle. Then lever 50 is returned to the outer position shown in FIG. 1.

The surgeon then positions the instrument so that the pointed end 102 of the needle 100 is between the grooves 66A of the open jaws, and then returns the jaws to their closed position so that the pointed end of the needle is now grasped by the jaws. The instrument is then moved to pull the needle 100 fully out through the tissue, with the suture trailing along behind the needle and through the tissue. The needle is then grasped with a grasper or other suitable instrument (or the surgeon's fingers), and the jaws 62 are then again opened to release the needle. Lever 50 is then operated again to rotate the jaw assemblies back to their original position, i.e., lever 50 is returned to the outer position shown in FIG. 1. Then, the blunt end of the needle is again clamped by the jaws with the needle in the channel 48 formed by grooves 66B, and the foregoing procedure is repeated to perform a second suturing stitch operation.

FIG. 11 shows a different mode of attaching the jaw assemblies to arms 30A and 30B that eliminates use of retaining plates 86. In this case it will be seen that the cylindrical studs 76 may be formed with a constant diameter (although providing them with an enlarged head like head 78 shown in FIG. 3 also is acceptable). Also the blind holes 84 are modified by forming a smaller diameter hole 85 that intersects hole 84 and is conically flared as shown at 89. Additionally the outer ends of studs 76 are provide with threaded blind holes for receiving a screw 106 which has a tapered head for mating with the flared outer end 89 of the corresponding hole 85. The tapered heads of screws 106 are sized so as to make a loose fit in the flared outer end 89 of the corresponding holes 85, affording the screws 106 freedom to move axially and also to tilt a limited extent relative to arms 30A and 30B, so as to avoid any binding of the jaw assemblies when they are moved between open and closed position or when they are rotated as described above.

The mode of mounting the jaw assemblies to the arms 30A and 30B shown in FIG. 11 also may be practiced with the embodiment hereinafter described.

As noted previously, the embodiments described above are intended for "open" surgery wherein space availability generally is not as limited as in M.I.S. surgery.

FIGS. 13–23 illustrate an alternative embodiment designed specifically for M.I.S. surgery, although the same device may be used in open surgery if desired.

Figures 22, 23:
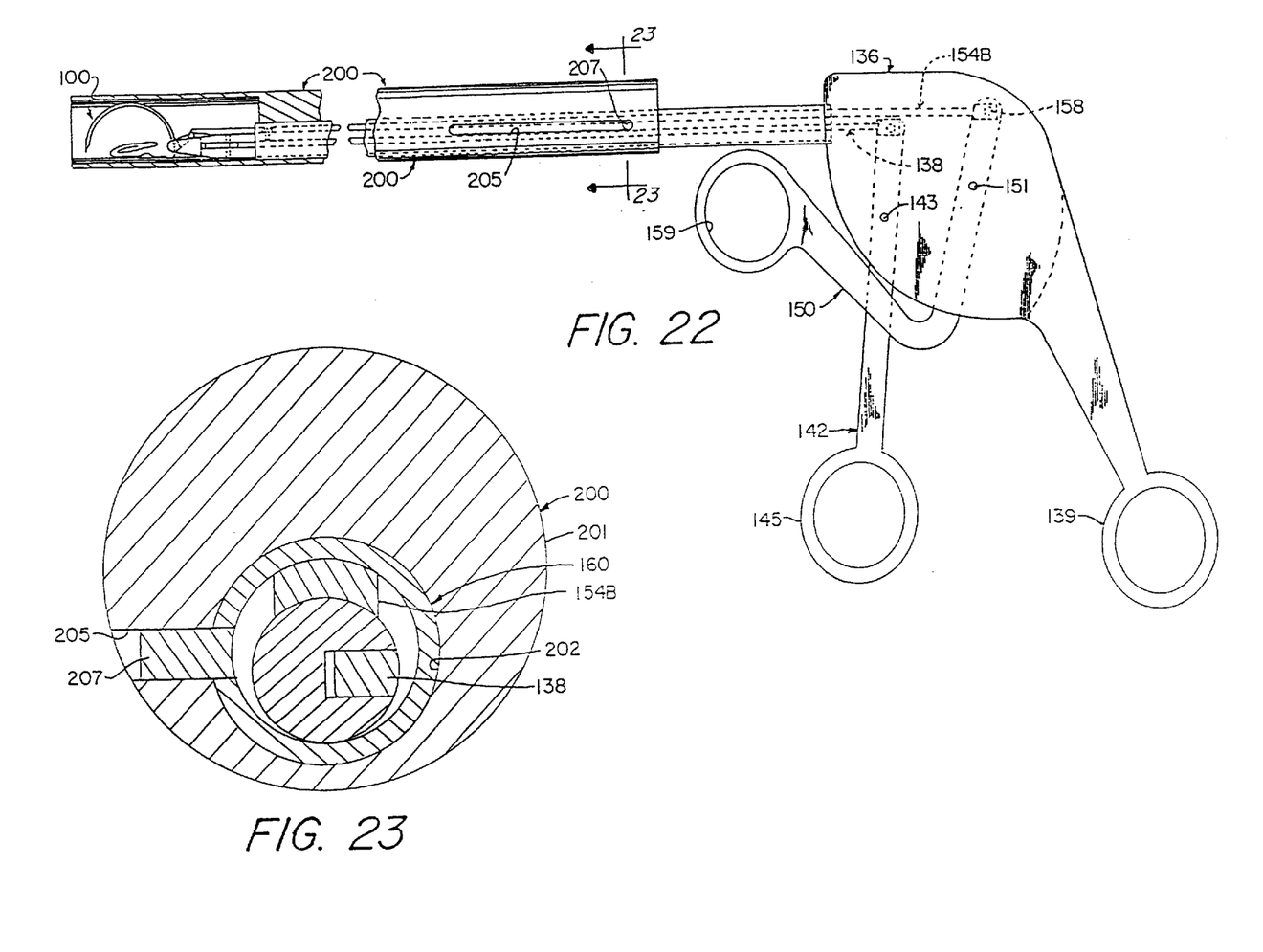
FIG. 22 is similar to FIG. 19 but illustrative also of the remainder of the instrument not shown in FIG. 19.
FIG. 23 is a sectional view taken along line 23—23 of FIG. 22.

Referring now to FIGS. 13–17, the illustrated instrument includes a first arm 130A having a lateral extension 131 that is pivotally connected to a second arm 130B by a pivot pin 134. The second arm 130B is elongate and is fixed to a handle member 136 (FIG. 22). Arm 130B is formed with a longitudinally-extending groove or channel 137 (FIG. 18). The first arm 130A also is pivotally connected by a pivot pin 146 to the distal end of a rod 138 which is slidably disposed in channel 137. Rod 138 projects rearwardly out of channel 137 and its proximal end is pivotally connected to a first arm operating means in the form of a lever 142. The latter is pivotally connected to handle member 136 by a pivot pin 143. The free end of lever 142 is formed with a finger grip, preferably in the form of ring handle 145. Handle member 136 has a similar ring handle 139. Surrounding second arm 130B and rod 138 is a cylindrical housing 160 which also is secured to handle member 136. Hence second arm 130B and housing 160 are fixed relative to one another, and rod 138 is movable axially relative to arm 130B and housing 160. As is obvious, pivotal movement of lever 142 relative to handle member operates to move the rod 138 axially in housing 160, whereby first arm 130A is caused to pivot relative to the second arm 130B and thereby move the distal ends of arms 130A and 130B toward or away from one another.

As in the embodiments shown in FIGS. 13–23, the arms 130A, 130B have mounted thereon jaw assemblies 140A and 140B which are identical to jaw assemblies 30A and 30B. Preferably the jaw assemblies 140A and 140B are mounted on the arms 130A and 130B in the same manner as described hereinabove with respect to the embodiment of FIGS. 1–10. Accordingly the components of the jaw assemblies and the means for mounting the jaw assemblies to arms 130A and 130B, including the blind holes in arms 130A and 130B for accommodating the heads 78 of studs 76, are identified in the drawings by the same numerals as are used to identify the corresponding components in FIGS. 1–10.

Figures 16, 18:
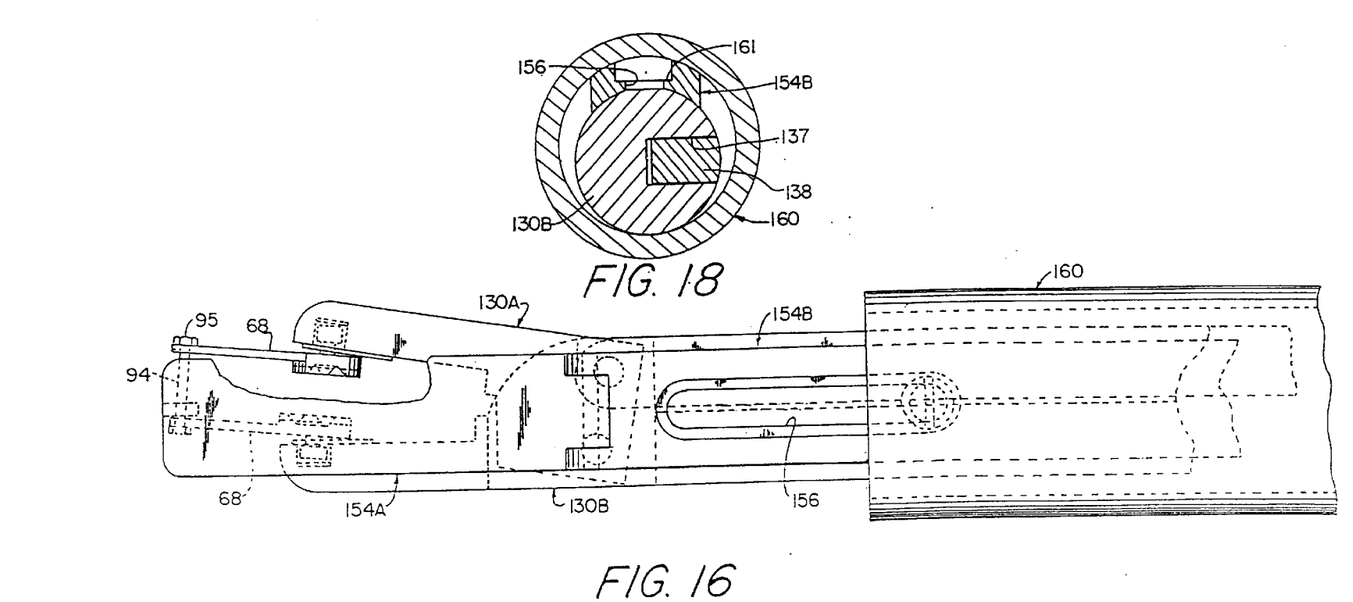
FIGS. 16 and 17 are side elevation views showing the jaw units in open but different rotational positions.
FIG. 18 is a sectional view taken along line 18—18 of FIG. 13.
Figure 17:
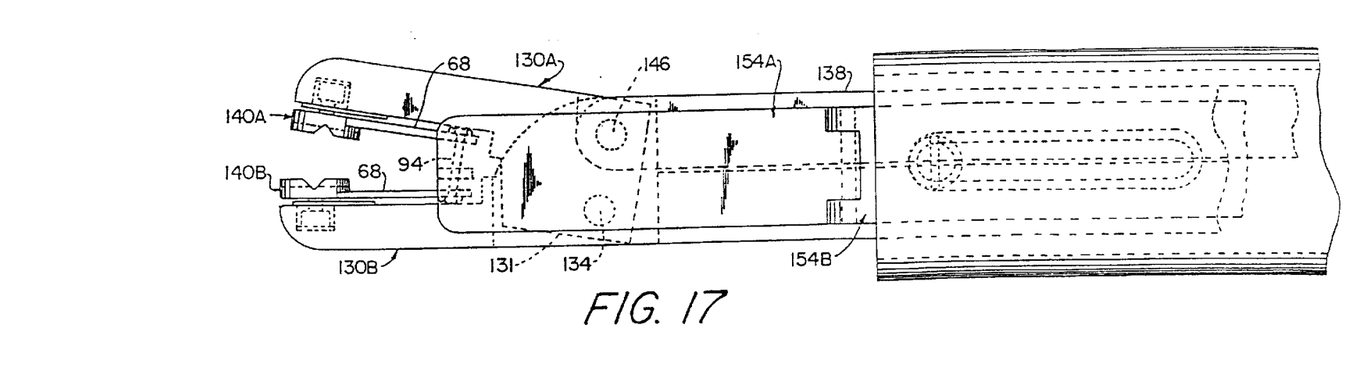

A drive lever assembly comprising drive lever 154A and a drive lever link 154B is provided for rotating the jaw assemblies. The distal end of drive lever 154A is pivotally connected to the outer ends of jaw links 68 by pivot pin 94 and nut 95 (not shown). The proximal end of drive lever 154A is connected to the distal end of drive lever link 154B by a pivot pin 155. Drive lever link 154B is slidably disposed within and extends lengthwise of housing 160. Preferably the outer surface of arm 130B has a cylindrical shape (except for groove 137) and drive lever link 154B has a similarly shaped inner surface that slidingly engages the outer surface of arm 130B, as shown in FIG. 18. Preferably also the outer surface of drive lever link 154B is curved so as to mate with and slidingly engage the inner surface of cylindrical housing 160. Driver lever link 154B has an elongate axially-extending stepped hole 156 which accommodates a retaining screw 157 that is screwed into a tapped hole in arm 130B. The head 159 of screw 157 makes a sliding contact with the shoulder 161 of hole 156, thereby keeping lever-link 154B flat against arm 130B while allowing it to undergo axial movement relative to that arm. The proximal end of drive lever link 154B is connected by a pivot pin 158 (FIG. 22) to a drive lever assembly operating means which may take various forms, but preferably is in the form of an operating lever 150 that is pivotally attached to handle member 136 by a pivot pin 151. The proximal end of operating lever 150 preferably is provided with a finger grip, as, for example, a ring grip 159.

To the extent already described, the instrument of FIGS. 12–23 is suitable for use in open surgery, and also in closed surgery by introducing the same to a surgical site via a cannula. However, in order to assure optimum operation and use, it is preferred to provide the instrument with a sheath that is adapted to shield a needle and suture held by the two jaws as they are being advanced to the surgical site, and then to expose the needle and sheath for the purpose of conducting a suturing procedure. Accordingly, with reference to FIGS. 19–23, a sheath member 200 is provided that preferably has a cylindrical outer surface 201 so as to facilitate its insertion and movement in a cylindrical cannula (not shown). Sheath member 200 has an eccentric axial bore 202 to accommodate housing 160. Bore 202 is sized to make a close sliding fit with housing 160. The forward (distal) end of sheath member 200 also has a large diameter center bore 203 (FIG. 20) that intersects eccentric axial bore 202. Bore 203 has a diameter large enough to accommodate a curved suture needle 100 that is held at its blunt or pointed end by the jaws 30A and 30B. Sheath member 200 also has an elongate hole 205 in its side wall (FIGS. 22 and 23), and housing 160 is provided with a radially-extending tapped hole in which is screwed a threaded retaining pin 207 that extends out through hole 205. Although not shown, the outer end of pin 207 has a kerf or shaped socket hole to accept a screwdriver, whereby pin 207 may be inserted or screwed. Pin 207 cooperates with hole 205 to limit axial movement of sheath member 200 relative to housing 160, the length of hole 205 being such that the sheath member can move from a first limit or retracted position in which its proximal end is engaged with or lies adjacent to the body portion of handle member 136 and the front (distal) end of the instrument (notably the two jaw assemblies and a suture needle grasped by the two jaws) projects from the front end of the sheath member, and a second limit or extended position (FIGS. 19, 20 and 22) in which the sheath member completely surrounds and shields the two jaw assemblies and a curved needle grasped by the two jaws.

Figure 19:
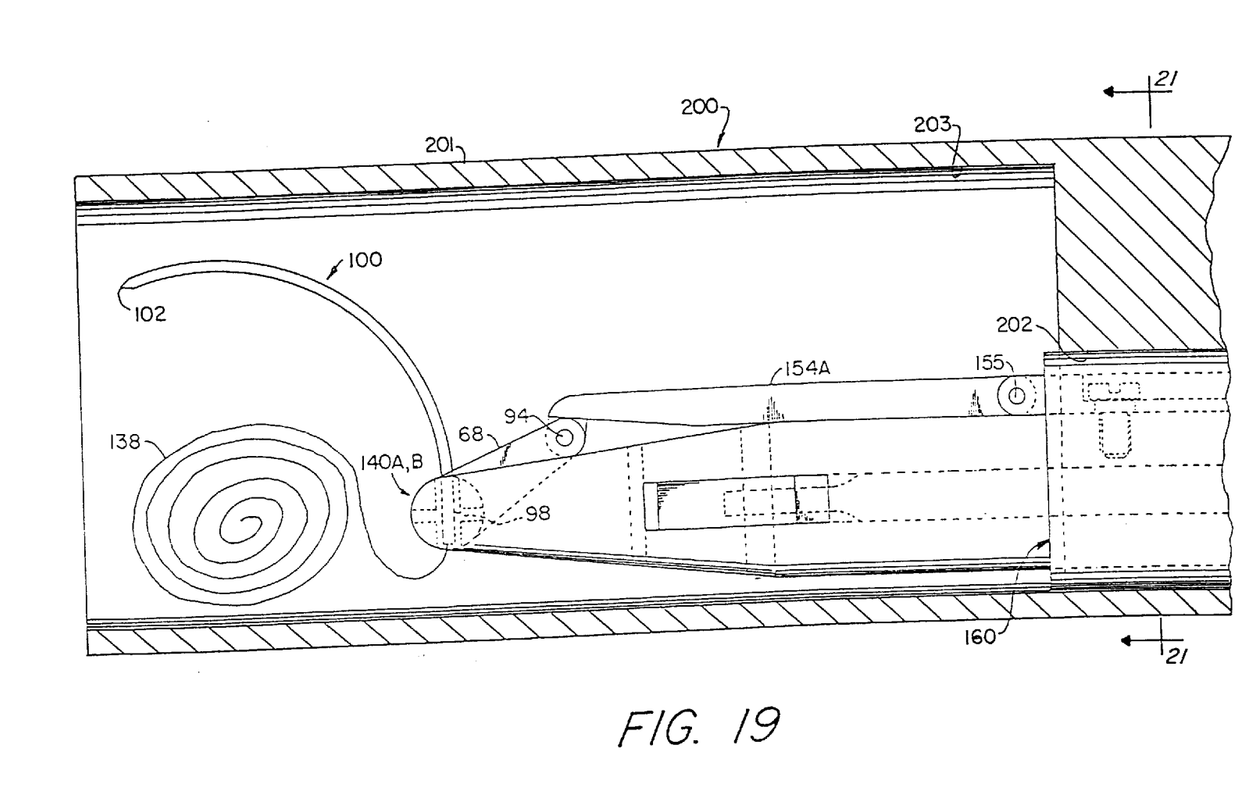
FIG. 19 is a partly sectional, partly elevational view similar to FIG. 13 but on a larger scale, showing the tail end of a suture needle grasped between the jaws and a sheath slidably mounted on the instrument in position to shield the suture needle when the needle is inserted into a cannula (not shown) for engagement with tissue at the surgical site.
Figures 20, 21:
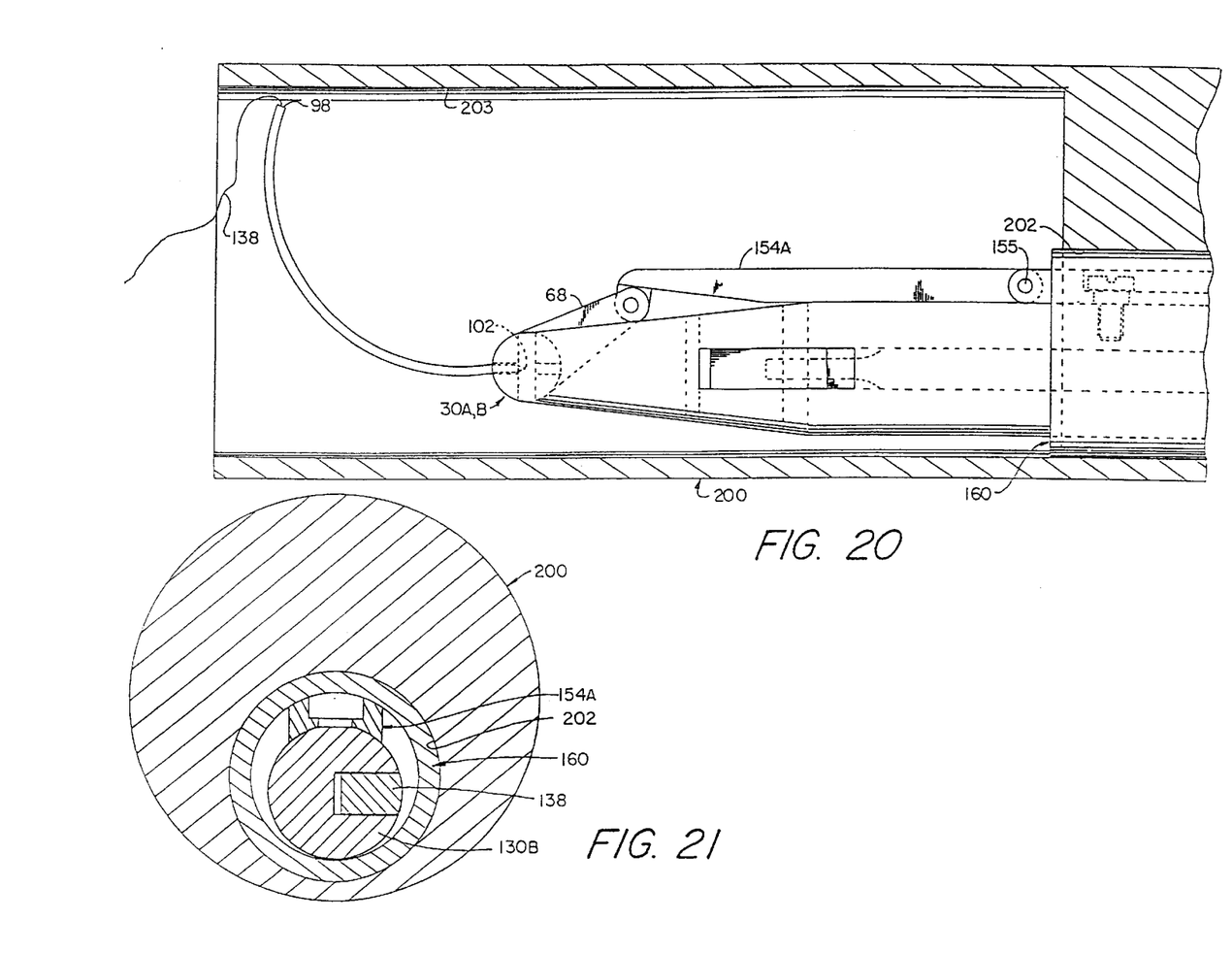
FIG. 20 is similar to FIG. 19, but showing the pointed end of the suture needle grasped by the device.
FIG. 21 is a sectional view taken along line 21—21 of FIG. 19.

Use of the M.I.S. surgery instrument of FIGS. 13–23 is similar to that of the instrument of FIGS. 1–10. With sheath 200 in retracted position, the jaw units 140A, 140B are closed upon the needle blunt end 98 of a needle 100, as illustrated in FIG. 19, with a suture 138 attached to needle 100. Also operating lever 150 is positioned as shown in FIG. 22, wherein the lever link 154B is in its retracted position and jaw assemblies 130A and 130B are in the position shown in FIGS. 19 and 22. The sheath member is then moved from its retracted jaw-revealing position to its extended needle-shielding position. Then the instrument is inserted into a cannula (not shown) that previously has been inserted into a person's body (note: the instrument also can be used for surgical procedures in the veterinary field). The instrument is inserted far enough to bring the sheath member close to the tissue that is to be sutured. Then the sheath member is retracted to expose the two jaw assemblies and the suture needle grasped by the two jaw assemblies. Next the pointed end 102 of needle 100 is engaged with the tissue sought to be sutured.

Figures 13, 14:
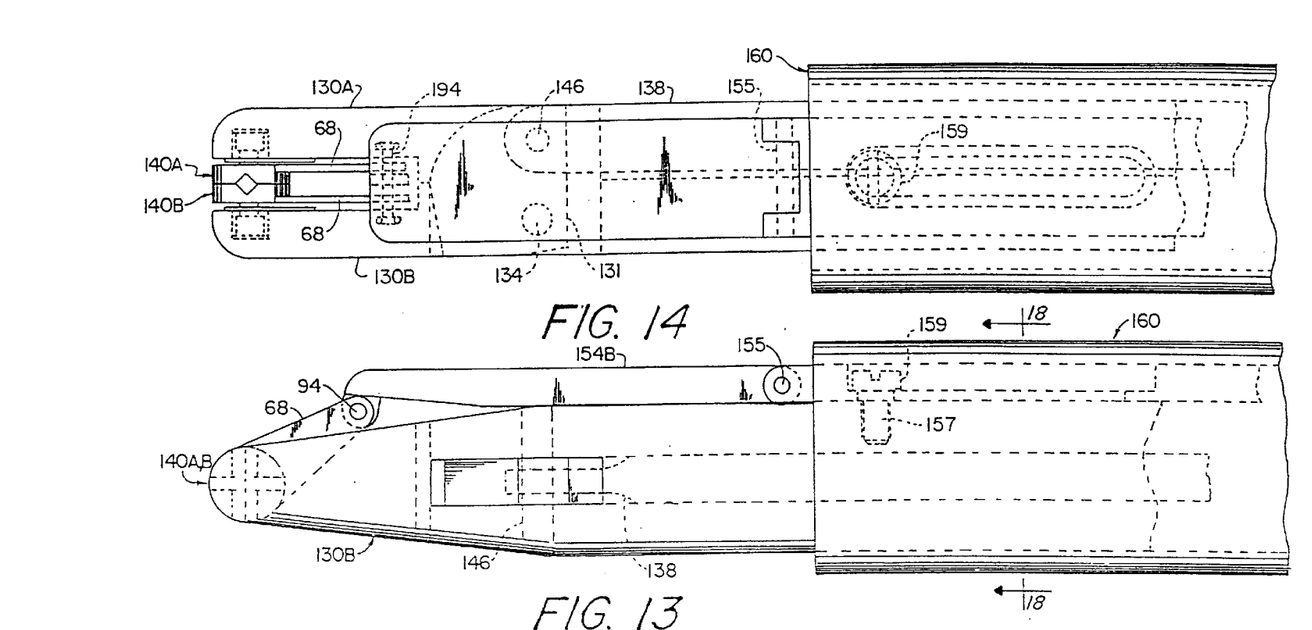
FIG. 13 is a plan view of a portion of another device that constitutes an alternative embodiment of the invention designed for laparoscopic surgery.
FIG. 14 is a side elevational view of the apparatus of FIG. 13.
Figure 15:
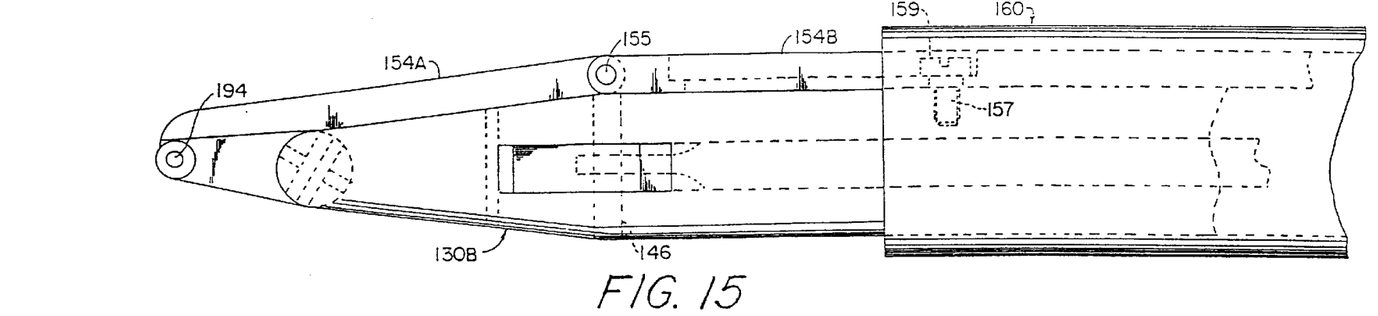
FIG. 15 is similar to FIG. 14, but showing the jaw units and jaw-rotating components in a different operative position.

Then lever 150 is pivoted so as to move drive lever link 154B forwardly from the position shown in FIGS. 19 and 22, whereby links 154B and 154A cause the two jaw assemblies 140A and 140B to pivot from the position shown in FIGS. 13 and 14 to the position shown in FIG. 15, thereby causing the needle to sweep in an arc similar to the movement of needle 100 from its solid line position to the dotted line position shown in FIG. 12, thereby forcing the needle to advance into, through, and in part back out of, the tissue. Thereafter the jaws are opened to release the needle. Then lever 150 is pivoted so as to move drive link 154B rearward to the position shown in FIG. 22. Then the instrument is positioned adjacent to the protruding pointed end of the needle, and the jaws are reclosed to grasp that pointed end. Then lever 150 is pivoted so as to move lever link 154B from the position shown in FIG. 22 to the position shown in dotted lines in FIG. 12, so as to pivot the needle free of the tissue. Then, with the needle grasped by another grasper (not shown) introduced via another cannula, lever 142 is moved to bring rod 138 rearward to open the jaws and release the needle. Then lever 150 is returned to its original forward position. Then the jaws are closed on the blunt end of the suture needle and the instrument is then ready for a repetition of the foregoing suturing steps.

It is to be understood that the present invention is by no means limited to the particular constructions herein disclosed and/or shown in the drawings, but also comprises any modifications or equivalents within the scope of the claims. Thus, for example, the number of grooves 66 in each jaw may be changed and also the faces 64 may be provided with other surface features for facilitating the gripping of a suture needle. Also, for example, the sheath 200 may be omitted. The form and shape of handle 136 and levers 142 and 150 also may be modified and the links or lever arms 68 may be formed separately from but affixed to jaws 62. Still other modifications will be obvious to persons skilled in the art.

What is claimed is:

1. A suture needle grasping and manipulating device comprising:

first and second arms each having a proximal end and a distal end;

first and second jaw units pivotally mounted on said distal ends of said first and second arms respectively;

means pivotally connecting said first arm to said second arm so as to permit relative pivotal movement of said arms between a first closed jaw position wherein said jaw units are in a closed position adjacent one another and a second open jaw position wherein said jaw units are spaced from one another far enough to permit a needle to be inserted between them;

a drive lever having a distal end and a proximal end;

means pivotally connecting said distal end of said drive lever to said jaw units so that axial movement of said drive lever will cause pivotal movement of said jaw units relative to said arms;

means attached to the proximal end of said drive lever for causing bi-directional axial movement of said drive lever so as to cause bi-directional pivotal movement of said jaw units relative to said arms; and means connected to said proximal ends of said arms for causing relative movement of said arms from one to the other of said first closed jaws position and said open jaws position;

said jaw units being adapted to releasably grasp and retain therebetween a suture needle, whereby pivotal movement of said jaw units relative to said arms while in said first closed jaw position will cause the suture needle to pivot in a corresponding direction for a stitching operation.

2. A device according to claim 1 wherein said means connected to said proximal ends of said arms are handles shaped for gripping by the fingers of a person's hand.

3. A device according to claim 2 wherein said means connected to said proximal end of said drive lever comprises an manually movable lever arm.

4. A device according to claim 3 wherein one end of said lever arm is pivotally connected to said drive lever and the opposite end of said lever arm is in position to be engaged and moved by a person's finger.

5. A device according to claim 1 wherein each of said first and second arms has a longitudinal axis and the pivot axis of said arms extends at a right angle to the longitudinal axis of each arm, and further wherein each of said jaw units has a pivot axis that extends at a right angle to the pivot axis of said arms.

6. A device according to claim 3 wherein said lever arm has a pivot axis that extends at a right angle to the pivot axis of said jaw units.

7. A device according to claim 5 wherein said lever arm has a pivot axis that extends parallel to the pivot axis of said first and second arms.

8. A device according to claim 1 wherein said first and second jaw units are connected to said first and second arms by first and second connections respectively that allow the pivot axes of said first and second jaw units to tilt relative to said first and second arms respectively.

9. A device according to claim 1 wherein the proximal end of each of said first and second arms is provided with a ring handle.

10. A device according to claim 1 further including means for locking said arms in a selected position relative to one another.

11. A suture needle grasping and manipulating device comprising:

first and second arms pivotally interconnected between proximal and distal ends thereof;

first and second jaw units pivotally mounted on said distal ends of said first and second arms respectively;

operating means attached to said arms at said proximal ends thereof for causing relative pivotal movement of said arms and thereby move said jaw units between a first closed position in which said jaw units are adjacent to one another so as to be able to grasp and retain a surgical needle and a second open position in which said jaw units are separated from one another far enough to permit a needle to be inserted between them;

a third arm pivotally mounted on one of said first and second arms; and a drive lever pivotally connected at a proximal end thereof to said third arm and pivotally connected at a distal end thereof to said first and second jaw units;

said drive lever being movable axially and bidirectionally by pivotal movement of said third arm so as to pivotally move said jaw units relative to said arms and thereby cause corresponding pivotal movement of a suture needle held between said jaw units, whereby to facilitate movement of said suture needle for a stitching operation.

12. A device according to claim 11 further including means for locking said arms in a selected position relative to one another.

13. A suture needle grasping and manipulating device comprising:

first and second arms each having a proximal end and a distal end;

first and second jaw units pivotally mounted on said distal ends of said first and second arms respectively;

means pivotally connecting said first arm to said second arm so as to permit relative pivotal movement of said arms between a first closed jaw position wherein said jaw units are in a closed position adjacent one another and a second open jaw position wherein said jaw units are spaced from one another far enough to permit a needle to be inserted between them;

a housing surrounding said second arm;

drive lever means, said drive lever means comprising a drive lever and a drive lever link, said driver lever and said driver lever link each having a distal end and a proximal end, and said drive lever link extending within said housing;

means pivotally connecting said distal end of said drive lever to said jaw units so that movement of said drive lever will cause pivotal movement of said jaw units;

means pivotally connecting the proximal end of said drive lever to the distal end of said drive lever link;

means connected to the proximal end of said drive lever link for causing reciprocal movement of said drive lever link, whereby to cause said drive lever to cause bidirectional pivotal movement of said jaw units relative to said arms;

means connected to said first arm for causing relative pivotal movement of said first and second arms so that said jaw units move from to one to the other of said first closed jaw position and said second open jaw position;

said jaw units being adapted to releasably grasp and retain therebetween a curved suture needle, whereby pivotal movement of said jaw units while in said first closed position will cause the suture needle to pivot in a corresponding direction for a stitching operation.

14. A device according to claim 13 wherein said means connected to said first arm for causing relative pivotal movement of said first and second arms comprises an elongate member that extends parallel to said second arm.

15. A device according to claim 13 wherein each of said first and second arms has a longitudinal axis and the pivot axis of said arms extends at a right angle to the longitudinal axis of each arm, and further wherein each of said jaw units has a pivot axis that extends at a right angle to the longitudinal axis of said arms.

16. A device according to claim 13 wherein said means connected to the proximal end of said driver lever link is a lever arm that has a pivot axis that extends parallel to the pivot axis of said jaw units.

17. A device according to claim 16 wherein said lever arm has a pivot axis that extends at a right angle to the pivot axis of said first and second arms.

18. A device according to claim 13 wherein said first and second jaw units are connected to said first and second arms by first and second connections respectively that allow the pivot axes of said first and second jaws to tilt relative to said first and second arms respectively.

19. A device according to claim 18 wherein said jaw units can undergo limited movement toward and away from said arms.

20. A suture needle grasping and manipulating device comprising:

first and second arms pivotally interconnected between proximal and distal ends thereof;

first and second jaw units pivotally mounted on said distal ends of said first and second arms respectively;

operating means attached to said arms for causing relative pivotal movement of said arms and thereby move said jaw units between a first closed position in which said jaw units are adjacent to one another so as to be able to grasp and retain a surgical needle and a second open position in which said jaw units are separated from one another far enough to permit a needle to be inserted between them;

a third arm pivotally mounted on one of said first and second arms and having a grip means on a proximal end thereof; and a drive lever pivotally connected at a proximal end thereof to said third arm and pivotally connected at a distal end thereof to said first and second jaw units;

said drive lever being movable axially and bidirectionally by said third arm so as to pivotally move said jaw units relative to said arms and thereby cause corresponding pivotal movement of a suture needle held between said jaw units, whereby to facilitate movement of said suture needle for a stitching operation.

21. A device according to claim 20 wherein each of said jaw units comprises a jaw having a face with a groove thereon for receiving a needle, a stud attached to said jaw, means coupling said stud to one of said first and second arms in a loose play connection, a link attached to said jaw and extending laterally of said stud, and means connecting said link to drive lever so that movement of said driver lever by said third arm will cause pivotal movement of said jaw unit relative to said one arm.

* * * * *

UNITED STATES PATENT AND TRADEMARK OFFICE
CERTIFICATE OF CORRECTION

PATENT NO.   : 5,843,100
DATED        : December 1, 1998
INVENTOR(S)  : John C. Meade It is certified that error appears in the above-indentified patent and that said Letters Patent is hereby corrected as shown below:

Claim 3, column 10, line 39, change the word "an" to the word -- a --.

Claim 7, column 10, line 53, change the numeral "5" to the numeral -- 6 --.

Claim 21, column 12, line 63 after the words "link to", insert the word -- said --.

Signed and Sealed this

Eleventh Day of May, 1999

*Attest:*

Q. TODD DICKINSON

*Attesting Officer*          *Acting Commissioner of Patents and Trademarks*